United States Patent
Sohn et al.

(10) Patent No.: US 7,642,389 B2
(45) Date of Patent: *Jan. 5, 2010

(54) ENERGY INTEGRATED PROCESSES INCLUDING ALKYLATION AND TRANSALKYLATION FOR MAKING DETERGENT RANGE ALKYLBENZENES

(75) Inventors: Stephen W. Sohn, Arlington Heights, IL (US); Mark G. Riley, Hinsdale, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/673,930

(22) Filed: Feb. 12, 2007

(65) Prior Publication Data

US 2008/0194893 A1 Aug. 14, 2008

(51) Int. Cl.
C07C 2/58 (2006.01)
C07C 6/12 (2006.01)
(52) U.S. Cl. .................. 585/323; 585/470; 585/450
(58) Field of Classification Search .................. 585/323, 585/470, 450
See application file for complete search history.

(56) References Cited

U.S. PATENT DOCUMENTS

| | | | | |
|---|---|---|---|---|
| 4,310,440 A | 1/1982 | Wilson et al. | ............... | 252/435 |
| 4,440,871 A | 4/1984 | Lok et al. | ................... | 502/214 |
| 4,774,377 A * | 9/1988 | Barger et al. | ................ | 585/323 |
| 4,793,984 A | 12/1988 | Lok et al. | ................... | 423/306 |
| 4,870,222 A | 9/1989 | Bakas et al. | ................ | 585/323 |
| 5,003,119 A | 3/1991 | Sardina et al. | ............. | 585/323 |
| 5,185,485 A | 2/1993 | Dyroff et al. | ................ | 585/446 |
| 5,196,574 A | 3/1993 | Kocal | ........................... | 562/94 |
| 5,574,198 A | 11/1996 | Radici et al. | ................ | 585/323 |
| 5,811,623 A | 9/1998 | Ryu et al. | | |
| 6,069,285 A * | 5/2000 | Fritsch et al. | ............... | 585/449 |
| 6,187,981 B1 | 2/2001 | Marinangeli et al. | ........ | 585/323 |
| 6,225,516 B1 | 5/2001 | Radici et al. | ................ | 585/323 |
| 6,315,964 B1 | 11/2001 | Knifton et al. | .............. | 422/190 |
| 6,589,927 B1 | 7/2003 | Kott et al. | .................... | 510/357 |
| 6,617,481 B1 | 9/2003 | Kulprathipanja et al. | .... | 585/323 |
| 6,689,927 B1 | 2/2004 | Frame et al. | | |
| 6,740,789 B1 | 5/2004 | Bozzano et al. | ............. | 585/323 |
| 6,872,862 B2 | 3/2005 | Bridges et al. | | |
| 7,459,593 B1 | 12/2008 | Krupa et al. | | |
| 2003/0040653 A1 | 2/2003 | Travers et al. | ............... | 585/466 |
| 2005/0177017 A1 | 8/2005 | Euzen et al. | ................ | 585/467 |
| 2006/0224030 A1 | 10/2006 | Euzen et al. | ................ | 585/467 |

OTHER PUBLICATIONS

Ganeshpure et al., Transalkylation of Benzenes with Heavy Alkylbenzenes, Consisting of Dialkylbenzenes and Diphenylalkanes ($C_{10}$-$C_{14}$ alkyl chains) Catalysed by Nafion-H, Indian Journal of Technology, vol. 31, Jul. 1993, pp. 503-506.

(Continued)

*Primary Examiner*—Thuan Dinh Dang
(74) *Attorney, Agent, or Firm*—Arthur E Gooding

(57) ABSTRACT

Integrated, energy efficient process for making detergent range alkylbenzenes use a combination of a low benzene to olefin feed ratio for alkylation, alkylbenzene refining system operation and a transalkylation of dialkylbenzene co-produced during alkylation is used to reduce energy costs per unit of alkylbenzene product.

10 Claims, 3 Drawing Sheets

OTHER PUBLICATIONS

Pujado, *Linear Alkylbenzene (LAB) Manufacture*, Handbook of Petroleum Refining Processes, Second Edition, 1996, pp. 1.53 to 1.66.

Cowley, M. et al., "Alkylation of Benzene with 1-Pentene over Solid Phosphoric Acid" *Ind. Eng. Chem. Res.* 2006, 45, pp. 7399-7408 (published on Web Oct. 6, 2006) 2006 American Chemical Society.

Nel, R.J.J. et al., "Selectivity Differences of Hexene Isomers in the Alkylation of Benzene over Solid Phosphoric Acid" *Ind. Eng. Chem. Res.* 2007, 46, pp. 2902-2906 (published on Web Mar. 27, 2007) 2007 American Chemical Society.

* cited by examiner

ENERGY INTEGRATED PROCESSES INCLUDING ALKYLATION AND TRANSALKYLATION FOR MAKING DETERGENT RANGE ALKYLBENZENES

FIELD OF THE INVENTION

This invention pertains to energy integrated processes for making detergent range alkylbenzenes, and particularly to such processes using a solid, acidic catalyst for benzene alkylation. In the processes of this invention, a combination of a low benzene to olefin feed ratio for alkylation, alkylbenzene refining system operation and a transalkylation of dialkylbenzene co-produced during alkylation is used to reduce energy costs per unit of alkylbenzene product.

BACKGROUND TO THE INVENTION

Alkylation of benzene with olefin of 8 to 16 carbon atoms produces alkylbenzenes that may find various commercial uses, e.g., alkylbenzenes can be sulfonated to produce detergents. As used herein, alkylbenzenes refers to phenylalkanes wherein the alkane group has between about 8 and 16 carbon atoms. Alkylbenzenes are produced as a commodity product in large-scale facilities, e.g. often in amounts of 50,000 to 200,000 metric tonnes per year per plant. In the alkylation process, benzene is reacted with an olefin the desired length to produce the sought alkylbenzene. The alkylation conditions comprise the presence of homogeneous or heterogeneous alkylation catalyst such as aluminum chloride, hydrogen fluoride, silica alumina or zeolitic catalysts and elevated temperature.

The alkylbenzene must meet stringent product specifications to be commercially acceptable. For instance, alkylbenzenes, to be desirable for making sulfonated surfactants, must be capable of providing a sulfonated product of suitable clarity, biodegradability and efficacy. The benzene content of the product should be relatively free from benzenes, e.g., less than about 1 part per million by weight (ppmw), and often less than about 0.5 ppmw. Also, desirable alkylbenzene products are relatively free, e.g., less than about 50, preferably less than about 5, ppmw, from byproducts such as dialkylbenzenes, oligomers of olefins, and the like (herein referred to as "heavies"). Additional considerations for commercial alkylbenzene products include the 2-phenyl content and linearity of the alkyl substituent. With respect to efficacy, alkylbenzenes having higher 2-phenyl contents are desired as they tend, when sulfonated, to provide surfactants having better detergency but less solubility if the 2-phenyl content becomes too high. Thus alkylbenzenes having a 2-phenyl isomer content in the range from about 25 to about 40 percent are particularly desired.

The catalysts are not selective and other reactions of olefins can occur to produce heavies, i.e., dimers and dialkylaryl compounds. Also, skeletal isomerization of the olefin can occur, resulting in a loss of selectivity to the sought alkylbenzene. The formation of dialkylaryl compounds is particularly problematic as the reaction approaches complete conversion of the olefin and the concentration of the alkylbenzene has thus increased thereby increasing the likelihood that an olefin molecule will react with an alkylbenzene molecule rather than benzene. Accordingly, typical processes use a large excess of benzene to reduce the molar ratio of the sought alkylbenzene to the olefin in the reactor. For homogeneous hydrogen fluoride catalyzed processes, the benzene to olefin ratio is generally in the range of 6:1 to 8:1. Solid catalysts are prone to generate more heavies. Hence, for these solid catalysts the mole ratio of benzene to olefin is typically greater than 15:1. For making alkylbenzenes with reduced skeletal isomerization, the benzene to olefin ratio is often in excess of 20:1 and sometimes as much as 30:1.

As the ratio of benzene to olefin increases, additional process costs are also incurred in the recovery and recycling of the unreacted benzene in the alkylation product. The refining system for alkylbenzene production is summarized in Pujado, *Linear Alkylbenzene (LAB) Manufacture*, Handbook of Petroleum Refining Processes, Second Edition, pp 1.53 to 1.66 (1996), especially pages 1.56 to 1.60. Especially for large-scale, commercial alkylation processes such as are used for the production of linear alkylbenzenes, capital and operating costs can be very important, and the addition of additional distillation steps can thus be undesirable. Of the distillations effected in the alkylbenzene refining system, the benzene distillation requires the highest heat duty. The distillation to separate alkylbenzene from heavies, including dialkylbenzene, is typically conducted under subatmospheric pressure and is energy intensive to maximize the recovery of alkylbenzene.

The commercial processes that use of hydrogen fluoride as the alkylation catalyst do benefit from the ability to use lower benzene to olefin ratios. However, the use and handling of hydrogen fluoride does provide operational concerns due to its toxicity, corrosiveness and waste disposal needs. Solid catalytic processes have been developed that obviate the need to use hydrogen fluoride. Improvements in these solid catalytic processes are sought to further enhance their attractiveness through reducing energy costs and improving selectivity of conversion while still providing an alkylbenzene of a quality acceptable for downstream use such as sulfonation to make surfactants. Particular attention has been addressed to improving solid catalyst performance to enable lower benzene to olefin ratios to be used. While much progress has been made, energy efficiency gains are still sought to enhance the economic attractiveness of solid catalytic processes.

A desire exists for an integrated alkylbenzene production facility that can employ a transalkylation unit operation in an economically viable manner to enhance production of alkylbenzenes.

SUMMARY OF BACKGROUND DISCLOSURES

The use of alkylation and transalkylation unit operations in the preparation of monoalkylated aromatics is well known. Often such processes have been particularly suggested for making ethylbenzene and cumene although broader disclosures have been made. See, for instance, U.S. Pat. No. 4,870,222, column 1, lines 30 to 34.

Specific suggestions for transalkylating heavies made in the alkylation of benzenes for detergent range alkylbenzenes include Ganeshpure, et al., *Transalkylation of Benzenes with Heavy Alkylbenzenes, Consisting of Dialkylbenzenes and Diphenylalkanes ($C_{10}$-$C_{14}$ alkyl chains) Catalysed by Nafion-H*, Indian Journal of Technology, Vol. 31, July 1993, pp. 503-506. Radici, et al., in U.S. Pat. No. 5,574,198 disclose a process for producing linear alkylbenzenes using an aluminum chloride catalyst. At column 3, lines 35 to 40, the patentees indicate that the heterogeneous catalytic phase makes possible a transalkylation of polyalkylated species.

Travers, et al., in U.S. Patent Application Publication US2003/0040653 disclose the use of a heteropolyacid catalyst for alkylation. At paragraph 0023 the applicants provide for the recycle of at least a portion of a fourth fraction from the alkylation product, which fraction contains polyalkylbenzene, to the reaction zone so as to be at least partially transalkylated. They also contemplate a separate transalkylation zone containing a different catalyst. See paragraph 0025.

Euzen, et al., in U.S. Patent Application Publication US2005/0177017 disclose the use of a catalyst based on silicated alumina for alkylation. At paragraph 0219 the applicants provide for the recycle of at least a portion of a fourth fraction from the alkylation product, which fraction contains polyalkylbenzene, to the reaction zone so as to be at least partially transalkylated. They also contemplate a separate transalkylation zone containing a different catalyst. See paragraph 0225.

Euzen, et al., in U.S. Patent Application Publication US2006/0224030 disclose the use of a catalyst based on silica-alumina for alkylation. At paragraph 0237 the applicants provide for the recycle of at least a portion of a fourth fraction from the alkylation product, which fraction contains polyalkylbenzene, to the reaction zone so as to be at least partially transalkylated. They also contemplate a separate transalkylation zone containing a different catalyst. See paragraph 0243.

SUMMARY OF THE INVENTION

By this invention, processes for making alkylbenzene of detergent range using solid, acidic catalysts are provided that achieve enhanced energy consumption while still yielding alkylbenzenes of high product quality. The processes are enabled by purposefully conducting the alkylation of benzene to yield higher than desired amounts of dialkylbenzenes by reducing the benzene to olefin ratio of the feed for alkylation, and by further integrating the alkylation product refining system for energy efficiency enhancement with respect to reducing the load on the benzene distillation in the refining system and allowing monoalkylbenzene to be contained in the higher boiling fraction from a distillation to separate alkylbenzene from heavies, including dialkylbenzene. At least a portion of the dialkylbenzene is subjected to transalkylation to provide incremental alkylbenzene.

In accordance with the broad aspects, the continuous, integrated process for preparing monoalkylbenzene by the alkylation of benzene with olefin having between about 8 and 16, preferably 9 to 14, carbon atoms, said olefin being contained in a feedstock with paraffin, in the presence of solid, acid alkylation catalyst comprise:

(a) subjecting the feedstock to alkylation conditions comprising a catalytically effect amount of said solid, acidic alkylation catalyst to provide an alkylation product wherein (i) the mole ratio of benzene to olefin is less than about 15:1 and sufficient to provide an alkylation product containing at least about 5, preferably at least about 6, say, about 7 to 10, mass percent dialkylbenzenes based upon the total dialkylbenzenes and monoalkylbenzene in said alkylation product and (ii) the alkylation product has a Bromine Index less than about 100;

(b) separating by distillation at least about 99.5, preferably at least about 99.9, percent of the benzene contained in said stream to provide at least one lower boiling fraction comprising benzene and a first bottoms stream comprising monoalkylbenzene, alkanes and dialkylbenzene;

(c) separating by distillation at least about 90, preferably at least about 95, mass percent of the alkane contained in said first bottoms stream to provide a lower boiling fraction comprising alkane and a second bottoms stream comprising monoalkylbenzene and dialkylbenzene;

(d) separating by distillation the second bottoms stream to provide a third bottoms stream comprising dialkylbenzenes and a lower boiling fraction comprising monoalkylbenzene, said third bottoms stream comprising at least about 2, preferably at least about 5 or 20, mass percent monoalkylbenzene;

(e) subjecting at least a portion of the third bottoms stream to transalkylation conditions comprising the presence of benzene, preferably in a mole ratio to dialkylbenzenes of at least about 2:1, say, about 4:1 to 100:1, and a catalytically effective amount of solid transalkylation catalyst, which conditions are sufficient to convert at least about 40 mole percent of the dialkylbenzene, to provide a transalkylation effluent containing monoalkylbenzene, dialkylbenzene and benzene; and (f) passing transalkylation effluent to step (b).

Thus, by using the combination of a low benzene to olefin ratio in the feed to the alkylation of step (a) with a transalkylation, the processes of this invention can materially reduce the heat duty required in the alkylbenzene refining system, especially the benzene distillation, yet the sacrifice in selectivity to alkylbenzene due to the use of the low benzene to olefin ratio is ameliorated by using a transalkylation to convert dialkylbenzene to monoalkylbenzene. The alkylbenzene product can be of desirable quality. Preferably paraffin is in at least a 6:1 mass ratio to olefin in the feed to the alkylation of step (a), in part, compensates for the loss of benzene as a heat sink during the exothermic alkylation reaction, thus enhancing linearity. By blending back the transalkylation effluent with the alkylation product as feed to the benzene distillation of step (b), the refined product, i.e., the lower boiling, monoalkylbenzene fraction from step (d), can still be of acceptable quality. Often, the linearity of the refined product is at least about 85 percent, say at least about 88, percent.

Since the transalkylation effluent is recycled to the benzene distillation of step (b), the heavies distillation of step (d) is operated to allow monoalkylbenzene to be contained in the heavies-containing fraction thereby saving energy costs without undue loss of alkylbenzene.

Preferably, the alkylation of step (a) is conducted in at least 2 reaction zones, at least one of which is on stream and at least one of which is off stream, and the off stream reaction zone is subjected to regeneration conditions including the presence of benzene to provide a spent benzene stream. In a further preferred embodiment, at least a portion of the spent benzene stream is used as benzene for the transalkylation.

PARAMETERS

Color

Figure 1:
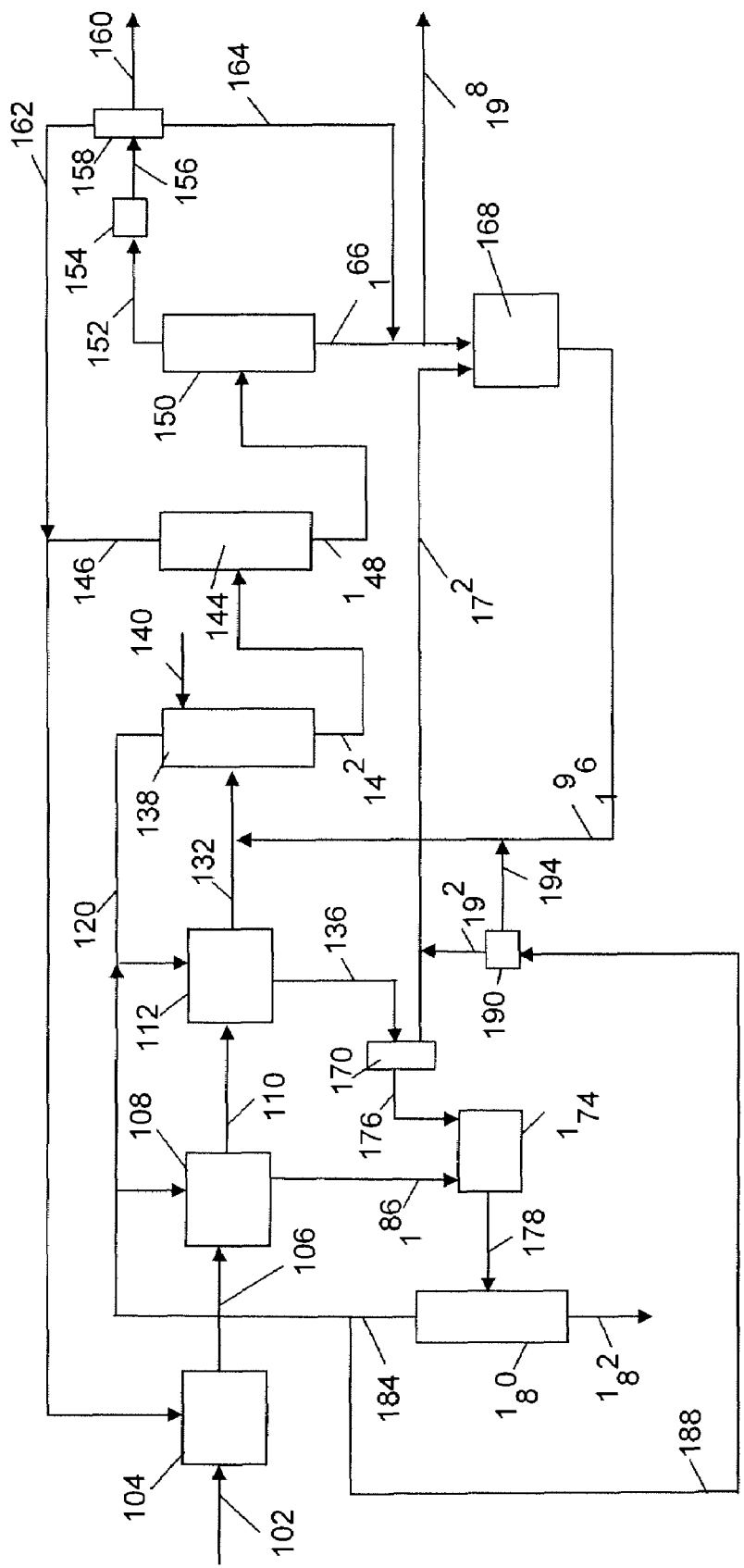
FIG. 1 is a schematic representation of an alkylbenzene complex using the processes of this invention.

As used herein, color bodies are components of a mixture that impart color to the mixture, and Saybolt color refers to Saybolt color as determined by ASTM D-156-00, Standard Test Method for Saybolt Color of Petroleum Products (Saybolt Chronometer Method), which is available from ASTM International, 100 Barr Harbor Drive, P.O. Box C700, West Conshohocken, Pa., USA.

Linearity

As used herein, linearity is the mass percent of normal alkylbenzenes to total alkylbenzenes.

Bromine Index

There are a number of methods for determining a bromine index of an alkylbenzene, but the methods often provide results that are not consistent with each other. Hence, for purposes herein, the bromine index is that measured by UOP Method 304-90, "Bromine Number and Bromine Index of Hydrocarbons by Potentiometric Titration", which is in effect on Jul. 31, 2004, available from ASTM International.

2-Phenyl Content

The 2-phenyl content of an alkylbenzene is the mass percent of the alkylbenzene that is a 2-phenylalkane.

DETAILED DISCUSSION

Various processes have been proposed for the alkylation of benzene. See, for instance, Pujado, *Linear Alkylbenzene (LAB) Manufacture*, Handbook of Petroleum Refining Processes, Second Edition, pp 1.53 to 1.66 (1996). One type of process uses a solid acidic catalyst involving contacting an olefin with a stoichiometric excess of benzene at elevated temperature to produce alkylbenzene. The reaction product stream will contain, in addition to alkylbenzene, benzene, some unreacted olefin, and reaction byproducts such as dialkylbenzene and oligomers and polymers of the olefin. For commercial processes, the feedstocks may include other components as well. For instance, the olefin may be obtained by the dehydrogenation of a paraffinic feedstock and thus contain significant amounts of paraffin.

The Olefin-Containing Feedstock

Olefin-containing aliphatic compound and benzene are used for the alkylation process. The selection of the olefin is dependent upon the sought alkylation product. The olefin-containing aliphatic compound is preferably has between about 8 and 16, and for detergent applications 9 to 14, carbon atoms. The olefin-containing aliphatic compound is an acyclic, mono-olefinic compound. The positioning of the olefinic bond in the molecule is not critical as most alkylation catalysts have been found to promote migration of the olefinic bond. However, the branching of the hydrocarbon backbone is often more of a concern as the structural configuration of the alkyl group on the alkylbenzene product can affect performance especially in surfactant applications and for biodegradation properties. For instance, where alkylbenzenes are sulfonated to produce surfactants, undue branching can adversely affect the biodegradability of the surfactant. On the other hand, some branching may be desired such as the lightly branched modified alkylbenzenes such as described in U.S. Pat. No. 6,187,981. The olefin may be unbranched or lightly branched, which as used herein, refers to an olefin having three or four primary carbon atoms and for which none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. Although branched, these alkylbenzenes have been characterized by their 2-phenyl content, see for instance, U.S. Pat. No. 6,589,927.

The olefin-containing aliphatic compound is usually a mixture of two or more olefins. For commercial processes, the feedstocks may include other components as well such as aromatics, lighter mono-olefins, diolefins, paraffins, halogenated hydrocarbons, and oxygenated hydrocarbons such as aldehydes, ethers, esters and carboxylic acids. For instance, the olefin may be obtained by the dehydrogenation of a paraffinic feedstock and thus contain paraffin. Of course, other olefin synthesis procedures such as dehydration of alcohols and dechlorination, can provide the olefin-containing feedstock. Feedstocks from such sources may have little, if any, paraffin.

The paraffin is inert in the alkylation reaction but it can serve an important function as a heat sink as the alkylation reaction is exothermic. Where lower benzene to olefin feed ratios are used, the importance of paraffins as heat sinks to adsorb the heat of the alkylation reaction, becomes more important. Accordingly, preferred olefin-containing feedstocks are those which have paraffin to olefin mass ratio of at least about 6:1. Often the feedstock comprises at least about 5 or 10 mass percent, and most frequently about 10 to 15, mass percent olefin.

Where the olefin is obtained by the dehydrogenation of paraffin, the source of the paraffinic feedstock is not critical although certain sources of paraffinic feedstocks will likely result in the impurities being present. Conventionally, kerosene fractions produced in petroleum refineries either by crude oil fractionation or by conversion processes therefore form suitable feed mixture precursors. Fractions recovered from crude oil by fractionation will typically require hydrotreating for removal of sulfur and/or nitrogen prior to being fed to the subject process. The boiling point range of the kerosene fraction can be adjusted by fractionation to adjust the carbon number range of the paraffins. In an extreme case the boiling point range can be limited such that only paraffins of a single carbon number predominate. Kerosene fractions contain a very large number of different hydrocarbons and the feed mixture to the subject process can therefore contain 200 or more different compounds.

The paraffinic feedstock may be at least in part derived from oligomerization or alkylation reactions. Such feed mixture preparation methods are inherently imprecise and produce a mixture of compounds. The feed mixtures to the process may contain quantities of paraffins having multiple branches and paraffins having multiple carbon atoms in the branches, cycloparaffins, branched cycloparaffins, or other compounds having boiling points relatively close to the desired compound isomer. The feed mixtures to the process of this invention can also contain aromatic hydrocarbons.

Another source of paraffins is in condensate from gas wells. Usually insufficient quantities of such condensate are available to be the exclusive source of paraffinic feedstock. However, its use to supplement other paraffinic feedstocks can be desirable. Typically these condensates contain sulfur compounds, which have restricted their use in the past. As this invention enables the use of sulfur-containing feeds, these condensates can be used to supply paraffins for alkylation.

Paraffins may also be produced from synthesis gas (Syngas), hydrogen and carbon monoxide. This process is generally referred to as the Fischer-Tropsch process. Syngas may be made from various raw materials including natural gas and coal, thus making it an attractive source of paraffinic feedstock where petroleum distillates are not available. The Fischer-Tropsch process is a catalytic process conducted under elevated temperature and pressure. The reaction is temperature sensitive, and temperature control is essential to achieve a desired hydrocarbon product. The products from the Fischer-Tropsch process include not only paraffins but also monoolefins, diolefines, aromatics and oxygenates such as alcohols, ethers, aldehydes and ketones, and thus are normally treated to eliminate oxygenates.

The olefin-containing feedstock should be sufficiently free of impurities that can unduly adversely affect the life of the alkylation catalyst and that can adversely affect the quality of the alkylbenzene product. The dehydrogenation of paraffins will result in a product containing aromatics, herein referred to as aromatic by-products. The aromatic by-products can comprise substituted phenyl compounds such as toluene, xylenes, and higher methylated benzenes; ethylbenzene, diethylbenzene, and triethylbenzenes; isopropylbenzene (cumene), n-propylbenzene, and higher propylbenzenes; butylbenzenes; and pentylbenzenes and the like; biphenyl compounds and substituted biphenyl compounds; and fused ring compounds and substituted fused ring compounds such as napthalenes, indanes, tetralins, and the like. Where the feedstocks are used to make alkylbenzenes and a paraffin-containing stream is generated during the purification of the alkylbenzenes and is recycled to the dehydrogenation, the feedstocks may also contain alkylbenzenes. In many instances, the aromatic by-products have the same carbon number as the mono-olefins. The concentration of the aromatic by-products can vary widely, e.g., from about 0.3 to 10 mass-percent based upon the mass of the feedstock.

Advantageously at least a portion of the aromatic by-products in the mono-olefin-containing feedstock is removed using at least one aromatics removal zone. An aromatics removal zone may be placed in one or more locations. For instance, where the feedstock is obtained from a catalytic dehydrogenation including a selective diolefin hydrogenation zone, the aromatic by-products may be selectively removed before or after the selective hydrogenation.

Suitable aromatics removal zones for this embodiment of the invention include sorptive separation zones. Sorptive separation zones include fixed bed or moving or fluidized sorbent bed systems, but the fixed bed system is preferred. The sorbent may be installed in one or more vessels and in either series or parallel flow. The flow of the feedstock containing the aromatic by-products through the sorptive separation zones is preferably performed in a parallel manner so that one or more sorption beds can be undergoing regeneration while one or more beds are removing aromatic by-products.

Suitable sorbents may be selected from materials which exhibit the primary requirement of selectivity for the aromatic by-products and which are otherwise convenient to use. Suitable sorbents include, for example, molecular sieves, silica, activated carbon activated charcoal, activated alumina, silica-alumina, clay, cellulose acetate, synthetic magnesium silicate, macroporous magnesium silicate, and/or macroporous polystyrene gel. It should be understood that the above-mentioned sorbents are not necessarily equivalent in their effectiveness. The choice of sorbent will depend on several considerations including the capacity of the sorbent to retain aromatic by-products, the selectivity of the sorbent to retain the aromatic by-products which are more detrimental to solid alkylation catalysts, and the cost of the sorbent. The preferred sorbent is a molecular sieve, and the preferred molecular sieve is 13 X zeolite (sodium zeolite X).

Those skilled in the art are able to select the appropriate conditions for operation of the sorbent without undue experimentation. For example, a fixed bed sorptive separation zone containing 13 X zeolite may be maintained at a temperature generally from about 20° C. to 300° C., and preferably from about 100° C. to 200° C., a pressure effective to maintain the stream containing the aromatic by-products in a liquid phase at the chosen temperature, and a liquid hourly space velocity from about 1 hr$^{-1}$ to about 10 hr$^{-1}$ and preferably from about 1 hr$^{-1}$ to about 3 hr$^{-1}$. The flow of the feedstock through a fixed or moving sorption bed may be conducted in an upflow, downflow or radial-flow manner.

Although both liquid and vapor phase operations can be used in many sorptive separation processes, liquid phase operation is preferred for the sorptive separation zone because of the lower temperature requirements and because of the higher sorption yields of the aromatic by-products that can be obtained with liquid phase operation over those obtained with vapor phase operation. Therefore, the temperature and pressure of the sorptive separation are preferably selected to maintain the feedstock in a liquid phase. The resulting unsorbed stream having a reduced concentration of aromatic by-products is a desorption effluent. However, the operating conditions of a sorptive separation zone can be optimized by those skilled in the art to operate over wide ranges which are expected to include the conditions in the reaction zones of the invention and its variants. Therefore, a sorptive separation zone may be contained in a common reaction vessel with the dehydrogenation zone, the selective diolefin hydrogenation zone, or the selective alkylation zone.

A sorbent bed is periodically subjected to regeneration conditions. A benzene-containing stream is use for the regeneration. Generally it is preferred that the benzene be highly pure to avoid undue sorption of any impurities on the sorbent during regeneration. Nevertheless, the regenerant may contain components that do not materially interfere with the regeneration and are acceptable in the sorption effluent. For integrated processes where the sorption effluent is used as a feed to a benzene alkylation reactor and benzene from the refining system is used as regenerant, to prevent undue buildup of paraffins in the regeneration effluent distillation system, the regenerant should contain less than 0.1 mass-percent paraffins, more preferably less than 100 mppm (mass part per million) paraffins. Typically the regenerant contains at least about 50, preferably at least about 90 or 99, more preferably to at least 99.5, to essentially 100, mass-percent benzene. A purge may be intermittently or continuously withdrawn from at least one point in the recycle loop consisting of the sorber assembly and the regeneration effluent distillation system in order to avoid excessive concentrations of paraffins. Where the sorption effluent is used as a feed to an alkylation reactor to make alkylbenzene, the regenerant is conveniently a pure benzene stream from the refining of the alkylbenzene-containing reaction effluent. Any suitable regeneration method may be used, including altering the temperature and pressure of the sorbent and treating with liquid or vaporous or mixed phase regenerant to displace or desorb aromatic by-products.

The spent benzene from the regeneration of the sorbent may be recycled to the alkylbenzene refining system or may be treated as disclosed in copending U.S. patent application Ser. No. 11/313,071, filed Dec. 20, 2005, herein incorporated by reference in its entirety.

The Alkylation

In the alkylation step, benzene and olefin feedstock are reacted under alkylation conditions to provide an alkylbenzene product. Alkylation conditions include the presence of a solid, acidic catalyst. The alkylation conditions selected will affect the nature of the alkylbenzene product as well as the conversion and selectivity to alkylbenzenes. For instance, higher alkylation temperatures can reduce the linearity of the alkylbenzene product and the type of catalyst can affect the 2-phenyl content of the alkylbenzene product. The benzene to olefin mole ratio is a major determinant of the extent of heavies generated during the alkylation.

Alkylation conditions generally include a temperature in the range between about 80° C. and about 200° C., most usually at a temperature not exceeding about 175° C. Since the alkylation is typically conducted in at least partial liquid phase, and preferably in either an all-liquid phase or at supercritical conditions, pressures must be sufficient to maintain benzene as a liquid. The requisite pressure necessarily depends upon the temperature, but normally is in the range of about 1300 to 7000 kPa(g), and most usually between about 2000 and 3500 kPa(g). Preferably the alkylation conditions do not result in substantial skeletal isomerization of the olefin. For instance, less than 15 mole percent, and preferably less than 10 mole percent, of the olefin, the aliphatic alkyl chain, and any reaction intermediate undergoes skeletal isomerization.

In accordance with this invention, a low mole ratio of benzene to olefin in the feed supplied to the alkylation is used. The ratio used will depend upon a number of factors including the sought balance between energy savings in the benzene distillation and the amount of dialkylbenzene that is to be subjected to transalkylation; the catalyst and other alkylation conditions used; and the arrangement of the alkylation zones, e.g., using a plurality of zones in series with intervening injection of olefin-containing feed to maintain in the feed to each zone, a high benzene to olefin ratio but a low benzene to olefin ratio in the feed to the alkylation unit operation over all. The mole ratio of benzene to olefin is less than about 15:1, and preferably is in the range of about 8:1 to 15:1, and sometimes between about 10:1 to 12:1.

Any suitable alkylation catalyst may be used in the present invention, provided that the requirements for conversion, selectivity, and activity are met. Alkylation catalysts comprise zeolites having a zeolite structure type selected from the group consisting of FAU, BEA, MOR, MTW, and NES. Such zeolites include mordenite, ZSM-4, ZSM-12, ZSM-20, ZSM-38, MCM-22, MCM-36, MCM-49, UZM-8, offretite, gmelinite, zeolite Y, NU-87, and gottardite. Another class of acidic, solid catalyst components are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315,964 and 6,617,481.

The catalyst may contain suitable binder or matrix material such as inorganic oxides and other suitable materials. The relative proportion of molecular sieve or other catalytically active component in the catalyst may range from about 10 to about 99 mass-percent, with about 20 to about 90 mass-percent being preferred. A refractory binder or matrix can be used to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria and silica. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO—Al_2O_3$ where M is a metal having a valence of 2; which components can be added to the composite at any suitable point.

Alkylation of benzene by the olefins is conducted in a continuous manner, i.e., both the benzene and the olefin-containing feedstock are continuously introduced into the alkylation zone containing the catalyst bed. For purposes herein, a catalyst bed is termed a reactor whether in the same or a separate vessel from another bed. The catalyst may be used as a packed bed or a fluidized bed. The feed to the reaction zone may be passed either upflow or downflow, or even horizontally as in a radial bed reactor. In one desirable variant, olefin-containing feedstock may be fed into several discrete points within the reaction zone.

One or more alkylation zones can be used. The alkylation zones may be configured in parallel with the same or different catalyst in each. Alkylation zones may also be configured in series, especially with a portion of the olefin-containing feedstock being fed to two or more alkylation zones. The benzene may be fed to the first reaction zone thereby providing a high benzene to olefin ratio in that zone, and the alkylation product is then fed, with additional olefin-containing feedstock to a subsequent reaction zone. Often 3 reactors are used to achieve an advantageous combination of performance and capital expense avoidance with one alkylation reaction zone being off-line for regeneration.

Where a low benzene to olefin ratio is used, there is less benzene to adsorb the heat of the alkylation reaction. As higher alkylation temperatures can result in loss of linearity of the alkylbenzene product can occur. It may be desired to use a plurality of alkylation zones with cooling there between. For instance, benzene and a portion of the olefin feedstock at a first blend temperature can be passed to a first zone where the mass ratio of benzene to olefin feedstock is sufficient that the temperature of the first zone effluent is less than 15° C., preferably less than about 12° C., and most preferably less than about 10° C., above the blend temperature; the first zone effluent is cooled and combined with another portion of the aliphatic feedstock at a second blend temperature. This mixture is passed to a second reaction zone to produce a second zone effluent comprising alkylbenzene and the mass ratio of benzene to olefin feedstock is sufficient that the temperature of the second zone effluent is less than 15° C., preferably less than about 12° C., and most preferably less than about 10° C., above the blend temperature. This technique can be repeated a sufficient number of times to use the olefin feedstock.

The cooling of each zone effluent may be by direct or indirect heat exchange, and is preferably at least partially effected by direct heat exchange with the portion of the olefin feedstock being passed to the zone, the olefin feedstock being provided at a cooler temperature than the preceding zone effluent. The cooling is often sufficient to reduce the temperature increased experienced in the previous reaction zone by at least 60 percent, and preferably the temperature reduction is at least to that of the blend temperature of the previous reaction zone.

A trim reaction zone containing solid alkylation catalyst can be used in any alkylation reaction scheme. The trim reaction zone does not receive any portion of the aliphatic feedstock but rather is maintained under liquid phase alkylation conditions sufficient to consume substantially all olefin contained in the zone effluent from the last of the zones.

Another technique is to remove at least a portion of the alkylbenzene between alkylation zones to reduce the production of dialkylbenzenes. The separation may be by any convenient means including membrane separation, selective sorption and distillation. In one technique a lights distillation is used to recover a portion of the unreacted benzene contained in the effluent from an alkylation reaction zone. The benzene is recycled to the alkylation zone, and the remaining portion of the unreacted aromatic compound is recovered in a subsequent distillation. The column size and energy requirements for the subsequent distillation are thus reduced.

Because the lights distillation need not provide a relatively pure aromatic stream, the energy requirements and size of the lights distillation can be commercially viable. Often, the lights distillation is effected using less than 5 theoretical distillation trays, especially a flash distillation. Thus, the overhead can contain appreciable amounts of alkylbenzene product as well as paraffins, if paraffins are present in the alkylation reactor effluent. Although arylalkane can be reacted to produce heavies under alkylation conditions, the processes of this invention can still provide an alkylation reaction effluent without an undue amount of heavies. Advantageously, the distillation is conducted at a lower pressure than the alkylation zone, and is often at between about 80 and 250 kPa absolute such that a significant portion of the aromatic compound in the at least a portion of the effluent fed to the first distillation zone, is vaporized.

Catalyst Regenerations

During use, the catalyst becomes deactivated. This deactivation is substantially reversible and thus the catalyst can be regenerated. Without intending to be limited to theory, it is believed that a significant portion of the deactivation occurs through the deposit of deactivating components on the catalyst and in its pore structure. Hence, when using two or more selective alkylation reactors, at least one is on-stream where alkylation occurs and at least one off-stream where catalyst regeneration takes place. Regeneration is effected by contacting the catalyst in the off-stream reactor with a stream comprising benzene.

After a reactor has been taken off-stream but before catalyst regeneration begins, the catalyst is typically purged, or flushed, to remove at least some of the unreacted monoolefins, paraffins, and alkylbenzene from the void volume of the now off-stream reactor. The purging conditions are not critical and may be any conditions that are effective for at least partially purging the void volume of the alkylation catalyst. Preferably the off-stream reactor purging conditions comprise at least a partial liquid phase.

The contacting conditions for purging the catalyst in the off-stream reactor can be the same throughout the off-stream reactor purging, although some changes could be made. The purging can be started by simply stopping the flow of the olefinic feed stream to the on-stream reactor, thereby taking the on-stream reactor off-stream. The contacting temperature is preferably low enough that the deactivating components on the catalyst are not removed. The temperature is usually between about 120° C. and about 170° C. The duration of the purge step can vary widely. The purging need not be complete prior to entering the subsequent step of ramping the temperature up to a suitable regeneration temperature. Often, the duration of the purge step will be determined by the use of the benzene from the purge step and by the cycle time for regeneration that is available. See, for instance, U.S. Pat. No. 6,740,789, herein incorporated by reference in its entirety.

After purging, catalyst regeneration can begin. The catalyst regeneration conditions are not critical to the success of this invention. The regeneration conditions can be any conditions that are effective for at least partially reactivating the alkylation catalyst. Although olefins may contact the catalyst bed during regeneration, preferably no olefins contact or pass to the catalyst during regeneration. Preferably the regeneration conditions comprise at least a partial liquid phase.

The contacting conditions can be the same throughout the regeneration, but typically some changes in conditions are made. Commonly, the contacting temperature is changed during regeneration.

Typically a heating stage is used to increase the temperature to that suitable for regeneration. Generally, the temperature is raised by from about 50° C. to about 200° C. above the temperature of the purging. Typically the regeneration is conducted at a temperature between about 200° C. and about the critical temperature of the aromatic feed compound (e.g., benzene), and preferably between about 220° C. and 270° C. The temperature may be ramped up steadily or can be increased step-wise with temperature holds. Any suitable method may be used to raise the temperature. One method is heating the benzene by indirect heat exchange and then passing it into the reactor.

As the temperature increases, the benzene-containing stream begins to remove deactivating components that accumulated on the surface of the catalyst and block reaction sites. Since some of the components are gum-like materials that have some color (i.e., are color bodies), the presence of these materials in the regeneration effluent may begin to lower its Saybolt color.

Once the desired temperature for regeneration is reached, usually a hold period follows. The period of time for the regeneration depends on the nature of the catalyst and the extent and nature of the catalyst deactivation, typically from about 2 to about 20 hours. As the catalyst becomes depleted in the deactivating components, the amount and concentration of these materials in the spent benzene regenerating stream will decline. The regeneration is typically deemed complete when the content of the deactivating components in the spent benzene regeneration stream drops to a relatively low level.

Finally the reactor is a cooled down. The inlet regeneration temperature is reduced from the temperature at the end of the second step to the alkylation temperature. The manner and rate of temperature decrease is not critical to the success of this invention. The temperature may be ramped down steadily or dropped step-wise with temperature holds.

Refining

The alkylbenzene effluent from an alkylation reactor generally has the components and concentrations as set forth in Table 1.

TABLE 1

| Component | Concentration (mass) | Typical Concentration (mass) |
|---|---|---|
| Alkylbenzene | 0.05 to 30% | 2 to 25% |
| Benzene | 33 to 99% | 40 to 75% |
| Total olefin | 0.00001 to 2% | 0.0001 to 1% |
| Total paraffin | 0 to 66% | 1 to 50% |
| Heavies | 0.001 to 10% | 0.5 to 2% |

Typically refining of the alkylbenzene product involves the use of a benzene distillation, a paraffin distillation and a heavy alkylate distillation, the benzene distillation is generally conducted with a bottoms temperature of less than about 300° C., preferably less than about 275° C., usually between about 230° and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column may contain any convenient packing or distillation trays, but most often trays such as sieve and bubble trays, are used. Often the assembly provides at least about 5, say 6 to 70, and preferably 20 to 50, theoretical plates. The reflux ratio (herein defined as the distillate to reflux weight ratio) is often in the range of about 2:1 to 1:10, preferably about 1.5:1 to 1:5. The bottoms stream from the benzene distillation generally contains less than about 1000 ppmw, preferably less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., preferably less than about 275° C., usually between about 250° C. and 275° C., and at a pressure at which overhead is provided of between about 5 and 110, preferably between about 10 and 50, kPa absolute. The column may contain any convenient packing or distillation trays, but most often sieve trays are used. Often the paraffins distillation assembly provides at least about 5, say 7 to 20, theoretical plates. The reflux ratio is often in the range of about 3:1 to 1:10, preferably about 1:1 to 1:3. The bottoms stream from the paraffins distillation generally contains less than about 10, preferably less than about 5, weight percent paraffins and preferably less than about 10, often less than about 1, ppmw benzene. Preferably, the bottoms stream contains between about 0.5 and 5, say about 1 to 5, weight percent paraffins. The paraffins distillation may occur in a single column or two or more distinct columns may be used.

The heavy alkylate distillation is generally conducted with a bottoms temperature of less than about 300° C., preferably less than about 275° C., usually between about 250° C. and 275° C., and at a pressure of between about 0.5 and 30, preferably between about 1 and 5, kPa absolute. The column may contain any convenient packing or distillation trays, but most often structured packing is used. Often the heavy alkylate distillation assembly provides at least about 5, say 10 to 30, and preferably 10 to 20, theoretical plates. The reflux ratio is often in the range of about 2:1 to 1:5, preferably about 0.2:1 to 1:1. The overhead from the heavy alkylate distillation generally contains less than about 2 weight percent, preferably less than about 1 weight percent, and sometimes less than about 0.1 weight percent, total heavies. The benzene content of the overhead stream is generally less than about 5, preferably less than about 1, ppmw and the paraffins content is often less than about 10 weight percent.

In some instances a finishing distillation may be used where a lights-containing overhead stream is provided, it is not essential that the paraffin distillation substantially remove all the paraffin from the alkylbenzene stream. Hence opportunities exist for energy savings. For instance, the amount of reboiler heat can be reduced as the internal reflux in the distillation column need not be as great as when the bottoms stream has a lesser concentration of paraffins. Also, for a given column, the capacity of the column can be increased, e.g., to debottleneck an existing refining system.

With respect to the heavy alkylate distillation column, the finishing column can remove, as a bottoms stream, heavies. Therefore the heavy alkylate column can be operated to permit significant amounts of heavies to be in the overhead. As with the paraffins distillation, the flexibility provided by these processes enables a reduction in reboiler duty for the heavy alkylate distillation. This reduction, in turn, reduces the reflux in the column thereby allowing more heavies to pass into the overhead stream. In addition to the reduction in reboiler heat duty that could be achieved, the capacity of a given distillation column can be increased.

The finishing distillation is generally conducted with a bottoms temperature of less than about 300° C., preferably less than about 275° C., usually between about 250° C. and 275° C., and at a pressure of between about 5 and 110, preferably between about 10 and 50, kPa absolute. The assembly may contain any convenient packing or distillation trays, but most often structured packing is used. Often the assembly provides at least about 2, say 5 to 20, theoretical plates. The mid-cut is generally taken from a point where at least 2, often at least 3, theoretical plates exist above and at least 2, often at least 3, theoretical plates exist below. Preferably the distillation assembly is a divided wall column or has an internal column with a dedicated reboiler. The finishing distillation assembly may also be two separate columns.

In some instances it may be desired to subject an alkylbenzene stream that contains olefinic components to a catalytic operation to improve bromine index, the alkylbenzene stream is passed to a catalytic conversion zone containing an acidic catalyst under olefin reduction conditions. The particular unit operation is not critical to the broad aspects of the invention and any suitable operation may be used.

A number of processes for improving the quality of alkylbenzenes and reducing olefin content have been proposed. The catalysts may be clay or molecular sieve (natural or synthetic). Included in the clays are smectites, laponite, saponite, and pillared clays. Filtrol F-24 (Engelhard Corporation, Iselin, N.J.) is a preferred clay. Molecular sieves include zeolites A, beta, L, S, T, X and Y and omega, mordenite, erionite, chabazite, boggsite, cloverite, gmelinite, offretite, pentacil molecular sieves having silica to alumina ratios greater than about 10, and SAPO (such as SAPO 5 and 41). Engelhard Corporation represents that Filtrol F-24 has a pH of about 3.5.

The bromine index reduction is typically conducted at temperatures between about 25° C. and 250° C., and most often between about 70° C. and 150° C., under a pressure sufficient to maintain the stream under liquid conditions, e.g., within the range of about 0.1 to 150 kPa absolute. The contact time with the catalyst is sufficient to provide the desired reduction in bromine index. For a fixed bed system, the weight hourly space velocity is typically in the range of about 0.1 to 20 $hr^{-1}$. The bromine index of the treated alkylbenzene stream is preferably below about 10. The bromine index reduction conditions also cause byproducts such as the formation of dialkylbenzene and benzene from alkylbenzene and form oligomers and polymers from olefinic components.

The effluent from the bromine index reduction is subjected to the fourth distillation to remove as an overhead, benzene, and heavies such as the dialkylbenzene and the oligomers and polymers from olefinic components.

Transalkylation

The bottoms from the heavy alkylate column can be recovered and used as a heavy alkylate product, or can be subjected to a further separation, e.g., by distillation to recover alkylbenzene contained therein, or can be subjected to a transalkylation in the presence of benzene to convert, e.g., dialkylbenzenes to monoalkylbenzene.

The transalkylation can be continuous or batch (semicontinuous). The transalkylation conditions including catalyst can vary widely. Typical catalysts include those having acidic functionality. Acidic catalysts comprise zeolites having a zeolite structure type selected from the group consisting of FAU, BEA, MOR, MTW, and NES. Such zeolites include mordenite, ZSM-4, ZSM-12, ZSM-20, ZSM-38, MCM-22, MCM-36, MCM-49, UZM-8, offretite, gmelinite, zeolite Y, NU-87, and gottardite. Another class of acidic, solid catalyst components are acidified refractory oxides such as chlorided, fluorided, or sulfated alumina, gallia, boria, molybdia, ytterbia, titania, chromia, silica, zirconia, and the like and combinations thereof. Clays such as beidellite clays, hectorite clays, laponite clays, montmorillonite clays, nontonite clays, saponite clays, bentonite clays and mixtures thereof and amorphous catalysts may also find utility.

If desired, the transalkylation catalyst may be metal stabilized. The metal component typically is a noble metal or base metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Preferably the metal component comprises rhenium. Suitable metal amounts in the transalkylation catalyst range from about 0.01 to about 10 mass-percent, with the range from about 0.1 to about 3 mass-percent being preferred, and the range from about 0.1 to about 1 mass-percent being highly preferred. In some instances, it may be desirable to modify the catalyst such as by sulfiding either in-situ or ex-situ.

The catalyst may contain suitable binder or matrix material such as inorganic oxides and other suitable materials. The relative proportion of molecular sieve or other catalytically active component in the catalyst may range from about 10 to about 99 mass-percent, with about 20 to about 90 mass-percent being preferred. A refractory binder or matrix can be used to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria and silica. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; which components can be added to the composite at any suitable point.

The transalkylation is conducted in the liquid phase with a benzene to total alkyl substituted benzenes ratio (Bz:TAB) of at least about 1:1. Often this ratio is between about 2:1 to 100:1. In general, higher Bz:TAB is preferred as the liquid flow assists in removing coke precursors from the catalyst, thereby enhancing time on stream prior to regeneration or replacement. Preferred Bz:TAB will depend upon the severity of the transalkylation conditions, the superficial liquid velocity in the catalyst bed and the conversion per pass. Typically, the Bz:TAB is within the range of about 20:1 to 80:1, say, 30:1 to 60:1. The spent benzene-containing regeneration stream may be used directly or may be subjected to a purification to remove undesirable components such as gums and coke precursors. The purification may be a selective sorption, membrane separation or, preferably, a distillation. Advantageously, adequate purification via a distillation may be obtained by a flash distillation or one containing up to about 5, preferably up to about 2, theoretical distillation plates and low reflux to feed ratios. The spent benzene-containing stream provides at least about 50 mass percent As stated above, the processes of this invention may use all or a portion of the spent benzene-containing regeneration stream as feed for transalkylation. Where a portion of the spent benzene-containing stream is used, it may be an aliquot portion or may be taken from select stages of the regeneration process. The regeneration of the alkylation catalyst proceeds in generally four stages, purge, heating stage, hold period and cool down period. The composition of the spent benzene-containing stream will vary by each stage. As the spent benzene stream from the purge stage contains paraffins, alkylbenzene, and heavies from the interstices of the catalyst bed, it can readily be used as a benzene source for the transalkylation. When the regeneration of the alkylation catalyst proceeds to stages where deactivating components are being removed, often the spent benzene can be used without intervening treatment such as a flash distillation, without undue adverse effects on the transalkylation catalyst stability or alkylbenzene product quality.

Conditions employed for transalkylation normally include a temperature of from about 130° C. to about 270° C., preferably from about 180° C. to 240° C. At higher temperatures, a greater amount of cracking occurs with increased co-production of lights i.e., aliphatic hydrocarbons having 9 and fewer carbon atoms. Also, the higher temperatures tend to result in loss of linearity of the alkylbenzene which is not desirable for alkylbenzenes to be used for sulfonation to detergents. Hence, the more preferred transalkylation temperatures are from about 190° C. to 220° C. Moderately elevated pressures broadly ranging from about 100 kPa to 10 MPa absolute are also used for transalkylation such that the reactants remain in the liquid state.

The transalkylation reaction can be effected over a wide range of space velocities, with higher space velocities enhancing the stability of the catalyst but at the expense of conversion of dialkylbenzenes to monoalkylbenzene. Often, the conversion of dialkylbenzenes in the feed to a transalkylation zone is less than about 60 mass percent, say, between about 20 and 50 mass percent. Weight hourly space velocity generally is in the range of from about 0.1 to about 30, and frequently between about 0.5 and 4, $hr^{-1}$. In general, lower space velocities are preferred with lower Bz:TAB's from the standpoint of catalyst stability. The adding of hydrogen is optional. If present, free hydrogen is associated with the feedstock and recycled hydrocarbons in an amount of about 0.1 moles per mole of TAB up to about 10 moles per mole of TAB. As the temperature for transalkylation is typically more severe than that used for the alkylation of benzene, isomerization of the alkyl groups is more prevalent. Since the ratio of dialkylbenzene to total alkylbenzenes from the alkylation reaction is typically low, the linearity of the combined alkylbenzenes, that from the alkylation and that from the transalkylation, is often at least about 85, preferably at least about 88, mass percent.

For purposes herein, a catalyst bed is termed a reactor whether in the same or a separate vessel from another bed. The catalyst may be used as a packed bed or a fluidized bed. The feed to the reaction zone may be passed either upflow or downflow, or even horizontally as in a radial bed reactor. In one desirable variant, olefin-containing feedstock may be fed into several discrete points within the reaction zone.

One or more transalkylation zones can be used. The transalkylation zones may be configured in parallel with the same or different catalyst in each. A preferred transalkylation process effectively uses the benzene by separating at least a portion of the benzene from at least one transalkylation zone and passing that benzene to one or more transalkylation zones as all or a part of the benzene. The separation, if by distillation, will result in some of the lights also being recycled and a continuous or intermittent purge may be required to maintain the lights at a suitable concentration, e.g., less than about 20, preferably less than about 10, volume percent of the separated benzene. Preferably the fraction containing the alkylbenzene will also contain benzene to assist in maintaining a steady state operation. One advantage with this preferred process using a separation unit operation associated with the transalkylation zone is that the amount of fresh benzene required is reduced while still being able to provide a high Bz:TAB.

With respect to the associated separation being a distillation (transalkylation distillation), the amount of effluent from one or more transalkylation zones that is directed to the transalkylation distillation may be as little as 20 weight percent of the total effluent or may comprise the entire effluent stream. Often at least about 50, and sometimes at least about 80, weight percent of the effluent is subjected to the transalkylation distillation. Where more than one transalkylation zone is used, the effluent from one or more of the zones can be fed to the transalkylation distillation.

In any event, sufficient fluid must be removed from the transalkylation zone and the transalkylation distillation loop to prevent an undue build-up of inerts or other impurities in the loop. Typically the concentration of lights in the alkylation zone is less than about 20 weight percent, and preferably less than about 10, weight percent. Only a portion of the benzene contained in the feed to the transalkylation distillation zone is intended to be recovered in the overhead. The amount of the aromatic compound recovered in the overhead is often between about 20 and 98, say, 50 to 70 or 90, weight percent of that in the distillation feed. The overhead may also contain lights.

Advantageously, the distillation equipment need not be extensive to effect such recovery, e.g., the distillation may be accomplished with less than about 5 theoretical plates. Moreover, the lights distillation is preferably conducted without significant reboiler heat. Preferably the sought recovery of benzene is accomplished by a flash distillation due to temperature of the effluent from the transalkylation zone without the need for a heat source. Where heat is supplied to the transalkylation distillation, e.g., to provide for internal reflux in a fractionation column, it preferably is less than about 40, more preferably less than about 30, kilocalories per kilogram of the feed to the transalkylation distillation. Where a reflux is used, the rate of external reflux (distillation feed to reflux, F/R) is preferably between about 0.1:1 to 2:1, more preferably between about 0.4:1 and 0.8:1, kilogram per kilogram of effluent fed to the transalkylation distillation zone.

The transalkylation distillation may be effected in an open vessel for a flash distillation or may contain suitable trays or packing for a fractionation. A flash distillation may contain a demister to prevent liquid carryover in the overhead. Heat to the lights distillation zone may be provided by indirect heat exchange at the bottom of the zone, or by withdrawing, heating and recycling to the base of the column a portion of the liquid contained at the bottom of the lights distillation zone. The transalkylation distillation will provide a higher boiling fraction containing alkylbenzene, heavies and benzene.

All or a portion of the transalkylation product (obtained either or both from the transalkylation zone or the separation) is passed to the benzene column of the refining section. Unreacted heavies, of course, will be recovered in the refining section and can be thus recycled to the transalkylation unit operation. Where the transalkylation is operated to achieve a low conversion per pass, say, 20 to 40 weight percent conversion of the dialkylbenzenes, a portion of the transalkylation product (obtained either or both from the transalkylation zone or the separation) can be passed to a transalkylation zone for further conversion. Since low conversion is acceptable, lower temperatures can be used to enhance the linearity of the alkylbenzene produced by the transalkylation.

In some instances it may be desired to regenerate the transalkylation catalyst. Any suitable regeneration conditions may be used. Conveniently, the regeneration is effected by passing through the catalyst bed benzene at elevated temperature. The benzene may be from any suitable source, especially a portion of the spent benzene-containing stream from the regeneration of the alkylation catalyst. The temperature for the regeneration should not be so high as to adversely affect the transalkylation catalyst. Usually the temperature is in the range of about 170° C. to 300° C., say, 190° C. to about 220° C. or 250° C. The duration of the regeneration may vary depending upon the extent of regeneration sought and the other conditions for the regeneration. Typically, the regeneration proceeds for at least about 1 hour, e.g., from about 4 to 50 hours. The spent regenerant can be disposed of in any suitable manner. The spent benzene-containing regenerant may be subjected to a flash distillation to remove high boiling impurities such as carbonaceous deposits and precursors, and then passed to the benzene distillation in the alkylbenzene refining system.

THE DRAWINGS

The drawings are provided in illustration of an embodiment of the invention and are not in limitation thereof.

FIG. 1 schematically depicts an alkylbenzene complex 100 including the dehydrogenation of paraffin feedstock to make the olefin-containing feedstock for the alkylation. As shown, paraffin feedstock is supplied via line 102 to olefin production unit 104. Olefin production unit dehydrogenates paraffin and yields an olefin-containing feedstock which is withdrawn via line 106. Within olefin production unit 104 is not only a dehydrogenation reactor but also a distillation refining system and a selective hydrogenation unit operation to eliminate diolefins. The olefin-containing feedstock in line 106 contains predominantly paraffins, about 10 to 15 volume percent olefins and other co-boiling hydrocarbons including aromatics. Thus the feedstock is passed to selective sorption unit 108 for removal of aromatic impurities. The selective sorption unit 108 may be of any suitable design such as disclosed above. The selective sorption unit uses solid sorbent which can be regenerated with a benzene stream as will be discussed later.

Figure 2:
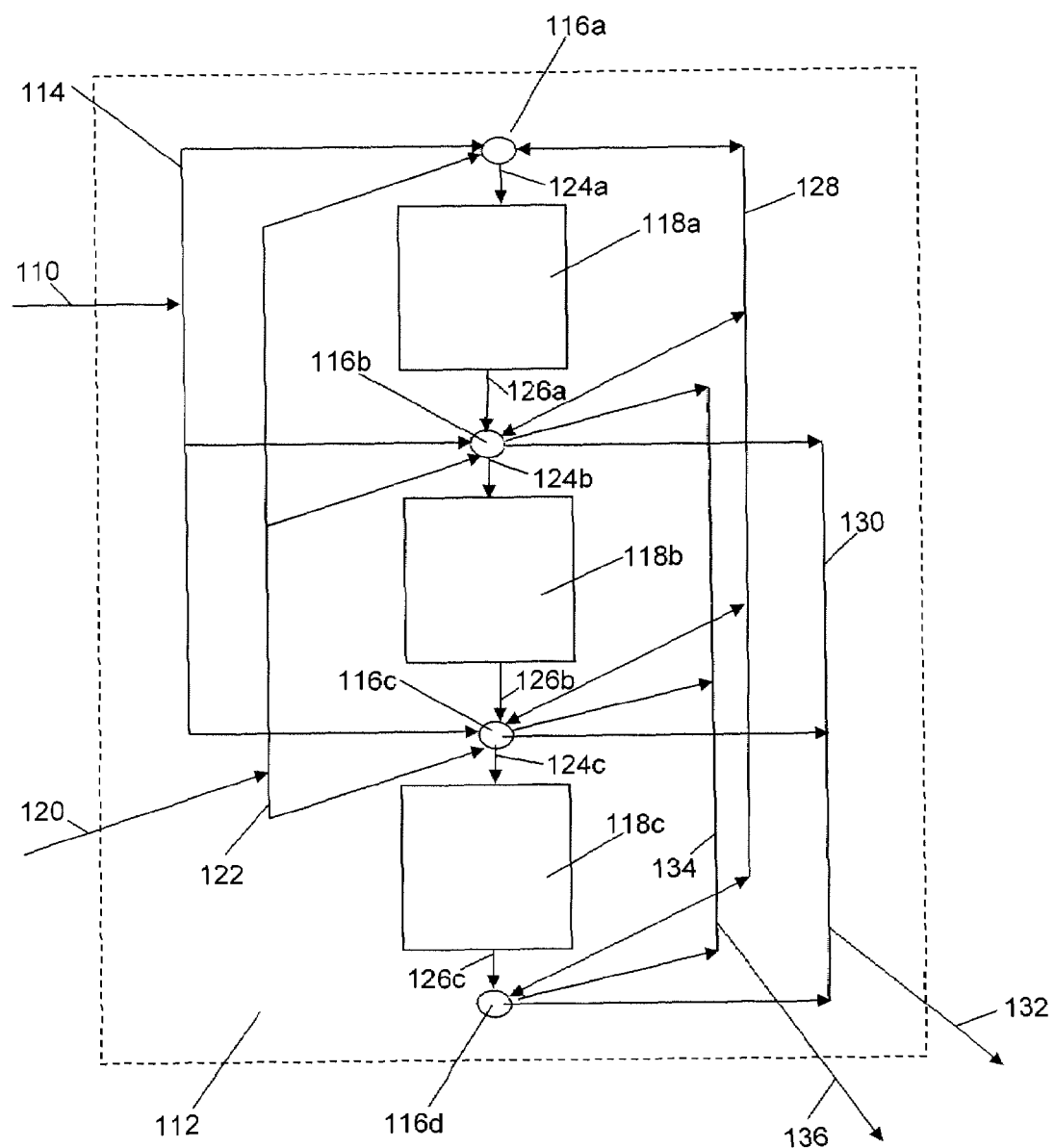
FIG. 2 is a schematic representation of an alkylation reactor assembly suitable for use in the alkylbenzene complex of FIG. 1.

The treated olefin-containing feedstock is then passed via line 110 to alkylation reaction assembly 112. Alkylation reaction assembly is discussed in connection with FIG. 2. In FIG. 2, the olefin-containing feedstock in line 110 is passed to olefin header 114 and then to control valve assemblies 116*a*, 116*b* and 116*c* associated with reactors 118*a*, 118*b* and 118*c*. Control valve assemblies may be one or more valves to control flows into and out of each reactor.

Benzene is supplied via line 120 to benzene header 122 which is in flow communication with each of control valve assemblies 116*a*, 116*b* and 116*c*. Each of control valve assemblies 116*a*, 116*b* and 116*c* are in fluid communication with reactors 118*a*, 118*b* and 118*c*, respectively via lines 124*a*, 124*b* and 124*c*. Reactors 118*a*, 118*b* and 118*c* are in fluid communication with the next sequential control valve assembly 116*b*, 116*c* and 116*d*, respectively via lines 126*a*, 126*b* and 126*c*. Each of control valve assemblies 116*a*, 116*b*, 116c and 116d are in fluid communication with internal flow header 128. Internal flow header 128 allows for the passage of a reactor effluent from one reactor to the inlet for another reactor. Each of control valve assemblies 116b, 116c and 116d are in fluid communication with alkylation effluent header 130 which in turn is in communication with line 132 for withdrawing alkylation effluent from alkylation reaction assembly 112. Each of control valve assemblies 116b, 116c and 116d are also in fluid communication with spent benzene header 134 which in turn is in communication with line 136 for withdrawing spent benzene from alkylation reaction assembly 112.

In operation, alkylation reactor assembly permits two reactors to be sequentially on stream while one reactor is undergoing regeneration and permits any of the reactors to be the first reactor in the series on stream. By way of illustration, olefin-containing feedstock in header 114 is partitioned by valve assemblies 116a, 116b and 116c to provide a portion of the feedstock only to reactors 118a and 118b. With reactor 118a being the first in the series, the control valve assemblies provide for benzene for the alkylation reactor to be all introduced into reactor 118a. Thus control valve assembly 118b permits no benzene from benzene header 122 from entering into reactor 118b. However, control valve assembly 116c permits benzene at a rate suitable for regeneration to be introduced into reactor 118c. The effluent from reactor 118a passes via line 126a to control valve assembly 116b. As reactor 118b is the next reactor in series, the effluent is directed via line 124b to reactor 118b. Control valve assembly directs the effluent from reactor 118b which is conveyed by line 126b to alkylation effluent header 130 to be withdrawn from reactor assembly 112 via line 132. Reactor 118c is undergoing regeneration and the spent benzene regenerant is passed via line 126c from reactor 118c to control valve assembly 116d which directs it to benzene purge header 134 and withdrawal from alkylation reactor 112 via line 136.

Upon completion of the regeneration of the catalyst in reactor 118c, it is placed back on-line and one of the other reactors is taken out of service for catalyst regeneration. Typically, the second reactor in the series on line is transitioned to regeneration. In such event, reactor 118c becomes the first reactor in the series and reactor 118a becomes the second in series. The control valve assembly appropriately changes the flows of the various streams. Thus, the benzene for the alkylation reaction is passed through valve assembly 116c and line 124c to reactor 118c while no benzene passes through valve assembly 116a. Benzene for regeneration is passed through valve assembly 116b and line 124b to reactor 118b. Olefin-containing feedstock is partitioned between valve assemblies 116a and 116c. The effluent from reactor 118c is passed via line 126c to valve assembly 116d to internal flow header which directs the effluent to valve assembly 116a to be passed to reactor 118a. Valve assembly 116b directs the effluent from reactor 118a to alkylation effluent header 130. The effluent from reactor 118b, which is being regenerated, is directed by valve assembly 116c to benzene purge header 134.

As can be seen from the above, each of the reactors can be cycled to different positions while on stream and taken off-stream for regeneration.

Returning to FIG. 1, alkylation effluent from reactor assembly 112 is passed via line 132 to benzene column 138 to provide a benzene-containing fraction which is recycled via line 120 to reactor assembly 112. Fresh benzene is provided via line 140 to benzene column 138. Not shown, but optional uses for the benzene-containing fraction from benzene column 138 is as a feed to the transalkylation reaction system and as a regenerant for the solid sorbent in selective sorption unit 108.

The bottoms fraction from benzene column, which contains alkylbenzene, heavies and paraffin is passed via line 142 to paraffins column 144. A lower boiling fraction rich in paraffins is passed via line 146 to olefin production unit 104. The bottoms fraction of paraffins column 144, which contains alkylbenzene and heavies is passed via line 148 to heavy alkylate column 150. Heavy alkylate column 150 provides a lower boiling fraction rich in alkylbenzene that is withdrawn via line 152. This fraction may also contain some benzene and paraffins as well as some olefinic components and thus a clay treater and finishing column are used. As shown, the lower boiling fraction in line 152 is passed to clay treater 154 and then via line 156 to finishing column 158. A side draw from finishing column 158 is taken via line 160 which is the alkylbenzene product. An overhead fraction containing paraffin and benzene is passed via line 162 to line 146 for ultimate recycling to olefins production unit 104. The bottoms fraction from finishing column 158 contains dialkylbenzene and is passed via line 164 for combination with the bottoms fraction from heavy alkylate column 150 which is withdrawn via line 166. The bottoms fraction from the heavy alkylate column contains heavies, i.e., dialkylbenzene, other heavier aromatics and olefin oligomers, and some alkylbenzene. The combined stream passes to transalkylation assembly 168. A stream may be split off via line 198 either as a purge to prevent undue build-up of heavy hydrocarbons or for further refining to provide a dialkylbenzene-containing product.

Returning to alkylation reactor assembly 112, spent benzene regenerant, which contains benzene as well as deactivating components removed from the catalyst, is passed via line 136 to distributor assembly 170. While not essential, distributor assembly directs the spent benzene regenerant that contains little color formers and gums directly to transalkylation assembly 168 via line 172. This spent benzene is from a purge of the reactor undergoing regeneration and thus contains alkylbenzenes, paraffin, and dialkylbenzene from the interstitial regions and from the catalyst surface and possibly some of the regenerant as the reactor cools down to temperatures suitable for alkylation. As the color formers and gums start to be removed from the regenerating catalyst, distributor 170 directs the spent benzene regenerant to hold tank 174 via line 176. Hold tank 174 serves as a reservoir for the spent benzene regenerant from which a constant flow of benzene can be withdrawn via line 178 for distillation in column 180.

A bottoms fraction containing higher molecular weight color formers and deactivating components is withdrawn via line 182 from column 180. A benzene fraction is withdrawn via line 184. As shown, a portion of the benzene fraction in line 184 is directed to selective sorption unit 108 as regenerant. The spent regenerant from selective sorption unit 108 is passed via line 186 to hold tank 174.

A portion of the benzene fraction in line 184 is passed via line 188 to valve assembly 190 which can direct all or part of the stream via line 192 to line 172 for the transalkylation assembly 168 and all or part of the stream via line 194 to line 196 which is in communication with benzene column.

Figure 3:
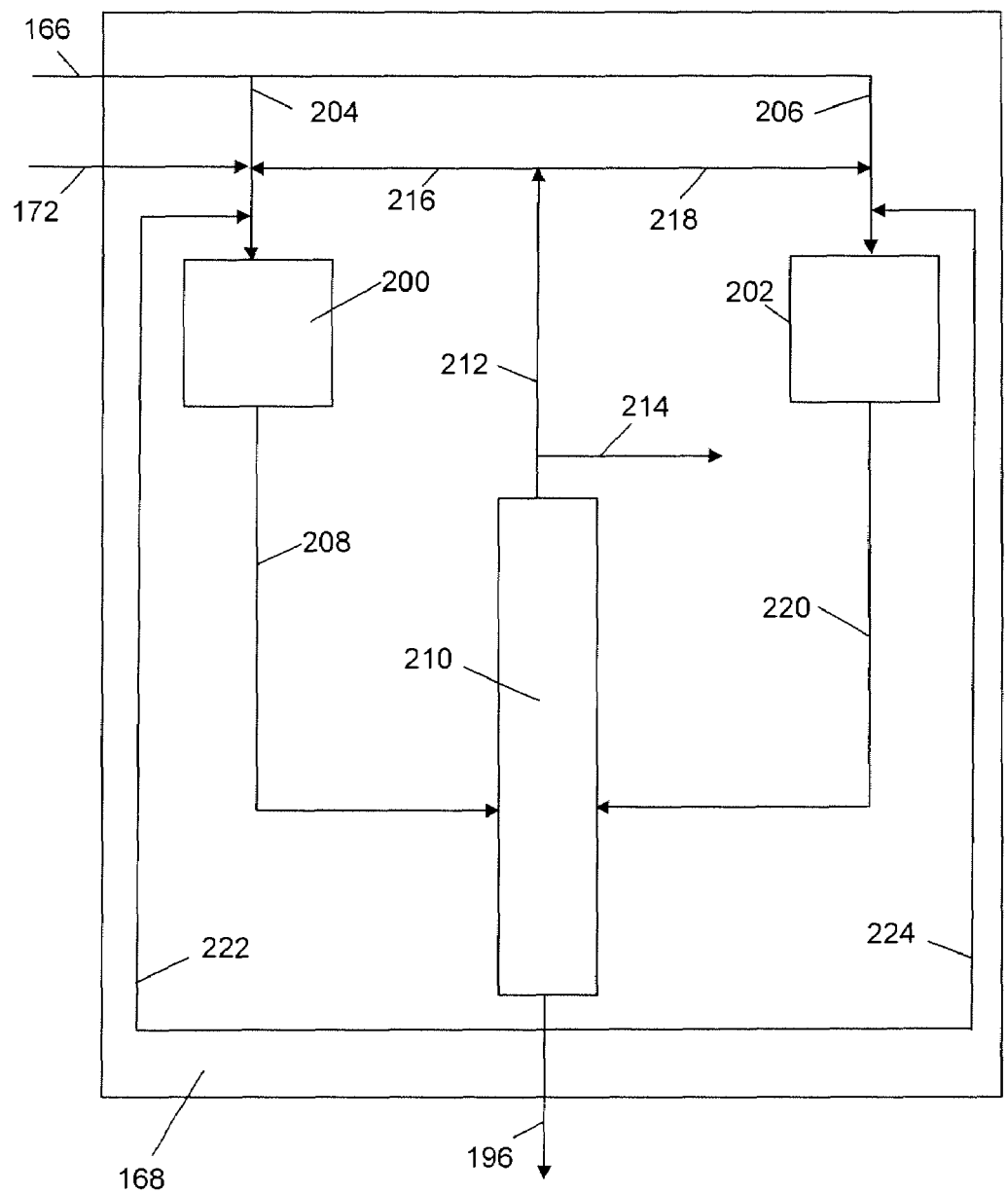
FIG. 3 is a schematic representation of a transalkylation assembly suitable for use in the alkylbenzene complex of FIG. 1.

Transalkylation assembly 168 is described further with reference to FIG. 3. The combined bottoms fraction from heavy alkylate column 150 and from finishing column 158 is passed to transalkylation assembly 168 via line 166, and a portion of the stream is directed to each of reactors 200 and 202 via lines 204 and 206, respectively. The make-up benzene is supplied by line 172 to line 204 and is passed to transalkylation reactor 200. The transalkylation effluent is withdrawn from reactor 200 via line 208 and supplied to stripping column 210 which serves to provide a benzene-containing fraction in line 212. A purge of the benzene-containing fraction can be effected via line 214. This purge can be passed to the benzene column, used for fuel value or exhausted from the complex. As shown, a portion of the benzene-containing fraction can be recycled, if desired, to reactor 200. The balance of this fraction is passed via line 218 to serve as the benzene for the transalkylation in reactor 202. Alternatively, part of the make-up benzene in line 172 can be passed to reactor 202. The effluent from reactor 202 is passed via line 220 to stripping column 210.

The bottoms fraction from stripping column 210 contains alkylbenzene produced by the transalkylation, unreacted dialkylbenzene, other heavies and a portion of the benzene. The bottoms fraction is withdrawn via line 196 and passed to benzene column 138 where benzene is recovered. The remaining unit operations in the refining section recover alkylbenzene, paraffin and return dialkylbenzene to the transalkylation assembly. If desired, a stream can be removed from line 196 and recycled to reactors 200 and 202 via lines 222 and 224, respectively for further conversion of unreacted dialkylbenzene.

It is claimed:

1. A continuous, integrated process for preparing monoalkylbenzene by the alkylation of benzene with olefin having between about 8 and 16 carbon atoms, said olefins being contained in a feedstock with paraffin, in the presence of solid, acid alkylation catalyst, the process comprising:
   (a) subjecting unbranched and lightly branched olefins in the feedstock to alkylation conditions comprising contacting a solid, acidic alkylation catalyst with the olefins without substantially isomerizing the olefins to provide an alkylation product wherein (i) the mole ratio of benzene to olefin is less than about 15:1 and sufficient to provide an alkylation product stream containing at least about 5 mass percent dialkylbenzenes based upon the total dialkylbenzenes and monoalkylbenzene in said alkylation product and (ii) the alkylation product has a Bromine Index less than about 100 and wherein the alkylbenzenes have a linearity of at least 85%, wherein the catalysts are selected from the group consisting of zeolites, acidified refractory oxides, and mixtures thereof, wherein the zeolite is selected from the group consisting of beta, mordenite, ZSM-4, ZSM-12, ZSM-20, ZSM-38, MCM-22, MCM-36, MCM-49, UZM-8, offretite, gmelinite, zeolite Y, NU-87, and gottardite, the acidified refractory oxides selected from the group consisting of chlorided, fluorided, or sulfated alumina, gallia, boria, molybdia, ytterbia, titania, chromia, silica, zirconia, and mixtures thereof;
   (b) separating by distillation at least about 99.5 percent of the benzene contained in said alkylation product stream to provide at least one lower boiling fraction comprising benzene and a first bottoms stream comprising monoalkylbenzene, alkanes and dialkylbenzene;
   (c) separating by distillation at least about 90 mass percent of the alkane contained in said first bottoms stream to provide a lower boiling fraction comprising alkane and a second bottoms stream comprising monoalkylbenzene and dialkylbenzene;
   (d) separating by distillation the second bottoms stream to provide a third bottoms stream comprising dialkylbenzenes and a lower boiling fraction comprising monoalkylbenzene, said third bottoms stream comprising at least about 2 mass percent monoalkylbenzene;
   (e) subjecting at least a portion of the third bottoms stream to transalkylation conditions comprising the presence of benzene, in a mole ratio to dialkylbenzenes of at least about 2:1, and a catalytically effective amount of solid transalkylation catalyst, which conditions are sufficient to convert at least about 40 mole percent of the dialkylbenzene, to provide a transalkylation effluent containing monoalkylbenzene, dialkylbenzene and benzene; and
   (f) passing transalkylation effluent to step (b);
   wherein the mixture of olefin and paraffin of step (a) is derived from the dehydrogenation of paraffin and a selective sorbent is used to remove aromatic compounds from the olefin and paraffin mixture prior to step (a) and at least a portion of recovered benzene is used to regenerate the selective sorbent and provide a spent regenerant stream.

2. The process of claim 1 wherein the mole ratio of benzene to olefin supplied to step (a) is sufficiently low that dialkylbenzene to total alkylbenzene and dialkylbenzene in the alkylation product is between about 7 and 10.

3. The process of claim 2 wherein the mole ratio of benzene to olefin supplied to step (a) is between about 8:1 to 15:1.

4. The process of claim 1 wherein the amount of alkylbenzene in the third bottoms stream is between about 5 or 20 mass percent.

5. The process of claim 1 wherein at least two alkylation zones are used and at any given time during the process, one of which is being regenerated with benzene to provide a spent benzene stream comprising benzene and heavies.

6. The process of claim 5 wherein the spent benzene stream is used as benzene for step (e).

7. The process of claim 1 wherein the mole ratio of benzene to total alkylbenzene and dialkylbenzene in step (e) is between about 4:1 to 100:1.

8. The process of claim 1 wherein the linearity of the alkylbenzene in the lower boiling fraction from step (d) is at least 85 percent.

9. The process of claim 1 wherein the mass ratio of paraffin to olefin in said feedstock is at least about 6:1.

10. A continuous, integrated process for preparing monoalkylbenzene by the alkylation of benzene with olefin having between about 8 and 16 carbon atoms, said olefin being contained in a feedstock with paraffin, in the presence of solid, acid alkylation catalyst, the process comprising:
   (a) subjecting the feedstock to alkylation conditions in an alkylation zone, where at least two alkylation zones are used and at any given time during the process, one of which is being regenerated with benzene to provide a spent benzene stream, and where the alkylation conditions comprise a catalytically effect amount of said solid, acidic alkylation catalyst to provide an alkylation product wherein (i) the mole ratio of benzene to olefin is less than about 15:1 and sufficient to provide an alkylation product containing at least about 5 mass percent dialkylbenzenes based upon the total dialkylbenzenes and monoalkylbenzene in said alkylation product and (ii) the alkylation product has a Bromine Index less than about 100 and wherein the alkylation product has a linearity of at least 85%, wherein the catalysts are selected from the group consisting of zeolites, acidified refractory oxides, and mixtures thereof, wherein the catalyst is selected from the group consisting of beta, mordenite, ZSM-4, ZSM-12, ZSM-20, ZSM-38, MCM-22, MCM-36, MCM-49, UZM-8, offretite, gmelinite, zeolite Y, NU-87, and gottardite, acidic or acidified refractory oxides selected from the group consisting of chlorided, fluorided, or sulfated alumina, gallia, boria, molybdia, ytterbia, titania, chromia, silica, zirconia, and mixtures thereof;

(b) separating by distillation at least about 99.5 percent of the benzene contained in said stream to provide at least one lower boiling fraction comprising benzene and a first bottoms stream comprising monoalkylbenzene, alkanes and dialkylbenzene;

(c) separating by distillation at least about 90 mass percent of the alkane contained in said first bottoms stream to provide a lower boiling fraction comprising alkane and a second bottoms stream comprising monoalkylbenzene and dialkylbenzene;

(d) separating by distillation the second bottoms stream to provide a third bottoms stream comprising dialkylbenzenes and a lower boiling fraction comprising monoalkylbenzene, said third bottoms stream comprising at least about 2 mass percent monoalkylbenzene;

(e) subjecting at least a portion of the third bottoms stream to transalkylation conditions comprising the presence of benzene derived from the spent benzene stream of step (a), in a mole ratio to dialkylbenzenes of at least about 2:1, and a catalytically effective amount of solid transalkylation catalyst, which conditions are sufficient to convert at least about 40 mole percent of the dialkylbenzene, to provide a transalkylation effluent containing monoalkylbenzene, dialkylbenzene and benzene; and (f) passing transalkylation effluent to step (b);

wherein the mixture of olefin and paraffin of step (a) is derived from the dehydrogenation of paraffin and a selective sorbent is used to remove aromatic compounds from the olefin and paraffin mixture prior to step (a) and at least a portion of recovered benzene is used to regenerate the selective sorbent and provide a spent regenerant stream.

* * * * *